(12) United States Patent
Kem et al.

(10) Patent No.: US 7,307,171 B2
(45) Date of Patent: Dec. 11, 2007

(54) MATERIALS AND METHODS FOR INHIBITING FOULING OF SURFACES EXPOSED TO AQUATIC ENVIRONMENTS

(75) Inventors: William Reade Kem, Gainesville, FL (US); Ferenc Soti, Gainesville, FL (US); Dan Rittschof, Morehead City, NC (US)

(73) Assignees: University of Florida, Gainsville, FL (US); Duke University, Durham, NC (US)

( * ) Notice: Subject to any disclaimer, the term of this patent is extended or adjusted under 35 U.S.C. 154(b) by 189 days.

(21) Appl. No.: 11/015,361

(22) Filed: Dec. 17, 2004

(65) Prior Publication Data

US 2005/0159454 A1 Jul. 21, 2005

Related U.S. Application Data

(62) Division of application No. 10/783,312, filed on Feb. 19, 2004, now Pat. No. 7,087,106.

(60) Provisional application No. 60/449,098, filed on Feb. 20, 2003.

(51) Int. Cl.
 *C07D 213/22* (2006.01)
(52) U.S. Cl. .................................... 546/257
(58) Field of Classification Search ................ 546/257
 See application file for complete search history.

(56) References Cited

U.S. PATENT DOCUMENTS

| | | | |
|---|---|---|---|
| 5,977,144 A | 11/1999 | Meyer et al. | |
| 6,509,469 B1 * | 1/2003 | Shintou et al. | ............. 546/252 |
| 6,603,007 B1 * | 8/2003 | Shintou | ...................... 546/257 |

FOREIGN PATENT DOCUMENTS

| | | |
|---|---|---|
| EP | 1 033 392 A | 9/2000 |
| GB | 1 514 651 A | 6/1978 |
| WO | WO 2004/058901 A | 7/2004 |

OTHER PUBLICATIONS

Patent Abstracts of Japan vol. 0173, No. 82 (C-1085), Jul. 19, 1993 & JP 5065433 A (Suzuki Sogyo Co. Ltd.), Mar. 19, 1993, abstract.
Database WPI, Section Ch, Week 197629, Derwent Publications Ltd., London, GB; Class C02, AN 1976-55047X & JP 51 063835 A (Kamata T) Jun. 2, 1976, Abstract.
Database WPI, Section Ch, Week 199140, Derwent Publications Ltd., London, GB; Class A21, AN 1991-290870 & JP 03 192167 A (Chugoku Toryo) Aug. 22, 1991, Abstract.
Hatt, H. and I. Schmiedel-Jakob (1984) "Electrophysiological studies of pyridine-sensitive units on the crayfish walking leg" *J. Comp. Physiol.* 154:855-863.
Kem, William R. (2002) In: Handbook of Neurotoxicology, E.J. Massaro, Ed. vol. 1 Humana Press, Totowa, NJ, pp. 161-193.
Kem, William R. (1988) "Pyridine alkaloid distribution in the hoplonemertines" *Hydrobiologia* 156:145-151.
Kem W. R. and Soti F., "Amphiporous Alkaloid Multiplicity Implies Functional Diversity: Initial Studies on Crustaciean Pyridyl Receptors" *Hydrobiologia* (2001), vol. 456, pp. 221-231.
Kem W., Abbott B., Coates R., "Isolation and Structure of a Hoplonemertine Toxin" *Toxicon* (1971), vol. 9, pp. 15-22.
Kem W., "A Study of the Occurrence of Anabaseine in Paranemertes and Other Nemertines" *Toxicon* (1971), vol. 9, pp. 23-32.
Kem W., Scott K., Duncan J., "Hoplonemertine Worms—A New Source of Pyridine Neurotoxins" *Experientia* (1976), vol. 32, pp. 684-686.
Matsushima, Sanji, Tomoko Ohsumi, Shiro Sugawara (1983) "Composition of Trace Alkaloids in Tobacco Leaf Lamina" *Agric. Biol. Chem.* 47(3):507-510.
Smith, C.R., C.H. Richardson, H. H. Shepard (1930) "Neonicotine and Certain Other Derivatives of the Dipyridyls As Insecticides" *J. Econ. Entomol.* 23:863-867.
Strausfeld, Nicholas J. and John G. Hildebrand (1999) "Olfactory systems: common design, uncommon origins?" *Curr. Rev. Neurobiol.* 9:634-639.
Warfield, A.H., W.D. Galloway, A.G. Kallianos (1972) "Some New Alkaloids from Burley Tobacco" *Phytochemistry* 11:3371-3375.
Zoltewicz, John A., Linda B. Bloom, William R. Kem (1990) "Hydrolysis of Cholinergic Anabaseine and N-Methylanabaseine: Influence of Cosolvents on the Position of the Ring-Chain Equilibrium-Compensatory Changes" *J. Bioorg. Chem.* 18:395-412.
Zoltewicz, John A., Linda B. Bloom, William R. Kem (1989) "Quantitative Determination of the Ring-Chain Hydrolysis Equilibrium Constant for Anabaseline and Related Tobacco Alkaloids" *J. Org. Chem.* 54:4462-4468.
Zoltewicz, J. A., Bloom, L. B., Kem, W. R., "N-Methylated 2,3'-Bipyridinium Ion. First Synthesis of the More Sterically Hindered Isomer" *J. Org. Chem.* (1992), vol. 57, pp. 2392-2395.

* cited by examiner

*Primary Examiner*—Patricia L. Morris
(74) *Attorney, Agent, or Firm*—Saliwanchik, Lloyd & Saliwanchik

(57) ABSTRACT

The subject invention provides materials and methods for inhibiting the biofouling of surfaces exposed to aquatic environments. In one embodiment, the subject invention provides additives for marine paints and surface treatments. The subject invention further provides repellents and selective inhibitors for aquatic and/or terrestrial crustacean pests.

1 Claim, 2 Drawing Sheets

Anabaseine 2,3'-Bipyridyl

Nemertelline

US 7,307,171 B2

MATERIALS AND METHODS FOR INHIBITING FOULING OF SURFACES EXPOSED TO AQUATIC ENVIRONMENTS

CROSS-REFERENCE TO A RELATED APPLICATION

This application is a divisional of application U.S. Ser. No. 10/783,312, filed Feb. 19, 2004, now U.S. Pat. No. 7,087,106 which claims the benefit of U.S. provisional patent application Ser. No. 60/449,098, filed Feb. 20, 2003.

GOVERNMENT SUPPORT

The subject matter of this application has been supported in part by U.S. Government Support under the National Oceanic Atmospheric Association Grant No. NA16RG2195. Accordingly, the U.S. Government has certain rights in this invention.

BACKGROUND OF INVENTION

A variety of organisms settle and colonize surfaces exposed to aquatic environments. These include bacteria, algae and sedentary invertebrates such as bryozoans, sponges, mollusks and barnacles. For example, barnacle larvae are major biofouling animals on marine surfaces. Encrusted barnacle populations increase the fuel requirements for ships, slow their passage and cause deterioration of the painted surface leading to corrosion.

Until now, efforts to inhibit the settlement of aquatic organisms have focused primarily on the inclusion of organotin paint additives that are toxic to a wide variety of aquatic organisms. With this strategy, the exposed surface must be scrapped and repainted at frequent intervals. Also, although organotin additives to marine paints are effective anti-fouling agents, unfortunately they also damage the marine environment, killing and sterilizing many free-living organisms where vessels are docked. The consequent pollution of harbors and coastal marine waters led to a ban on the use of such additives starting in 2003. Safer new antifouling additives are urgently needed to replace these toxic additives. Thus, there is much interest in finding new materials and methods to inhibit the colonization of surfaces by marine and other aquatic organisms.

It would be highly desirable to have anti-fouling additives that are more selective and more easily degraded such that they are less toxic. As the field evolves towards more selective and less toxic additives, one approach might be to exploit mechanisms associated with the process of settlement rather than with a broad spectrum biocide.

Little is known about the chemoreceptive capabilities of barnacle larvae, although knowledge of the chemoreceptors of other crustaceans is more advanced (Strausfield, N., Hildebrand, J. [1999] *Curr. Rev. Neurobiol.* 9:634-639). Besides being receptive to amino acids, some decapod crustacean neuronal chemoreceptors are sensitive to certain pyridine compounds, especially 3-substituted pyridines (Hatt, H., Schmiedel-Jakob I. [1984] *J. Comp. Physiol.* 154A:855-863; Hatt, H., Schmiedel-Jakob I. [1985] *Chem. Senses* 10:317-323; Schmiedel-Jacob I., Breuninger V., and Hatt H. [1988] *Chem. Senses* 13:619-632). Some of the most potent 3-pyridyls are natural toxins found in certain nemertines, a phylum of nearly 1,000 recorded species of carnivorous flatworms (Gibson, R. *Nemerteans*. London: Hutchinson University Library, 1972). Bacq (Bacq, Z. (1936) *Bull. Acad. R. Belg. Cl. Sci.* (Ser 5) 22:1072-1079) first demonstrated that nemertines possess toxins. Several decades later the alkaloid anabaseine (FIG. 1A) was isolated from a hoplonemertine (Kem W., Abbott, B., Coates, R. (1971) *Toxicon.* 9:15-22). Nemertines belonging to this taxonomic class were subsequently found to contain a variety of pyridyl alkaloids besides anabaseine (Kem, W. (1971) *Toxicon.* 9:23-32; Kem, W., Scott K., and Duncan J. (1976) *Exper.* 32:684-686; Kem, W. (1988) *Hydrobiolog.* 156:145-147; Kem, W. (2002) In: Handbook of Neurotoxicology, E. J. Massaro, Ed. Vol. 1. Humana Press, Totowa, N.J., pp.161-193). 2,3'-bipyridyl (BP) was identified as the major toxic constituent of the chevron nemertine *Amphiporus angulatus*, a circumboreal species found along northern Atlantic and Pacific coastlines (Kem, W., Scott K., and Duncan J. (1976), supra; Kem, W., Soti, F. (2001) *Hydrobiolog* 456:221-231). The worm uses its armed proboscis to mechanically capture and chemically paralyze its arthropod prey.

2,3'-BP (FIG. 1B) is the only bipyridyl that has been found in living organisms, namely tobacco plants and *A. angulatus*. However, 2,2'-BP, because of its ability to chelate certain heavy metals, is the most widely known BP. It is an important industrial product. The insecticidal activity of 2,3'-BP was noticed many decades ago, but apparently it was never marketed as an insecticide (Smith, C., Richardson, D., Shepard H. (1930) *J. Econ. Entomol.* 23:863-867). Some of the methyl-bipyridyls have been found in tobacco leaves and/or tobacco smoke. The 5-methyl-2,3'-bipyridyl was found in cured *Nicotiana tabacum* leaves (Warfield, 1972; Matsushima, 1983) as well as in cigarette smoke. The 6- and the 2'-(or 3-) methyl-2,3'-bipyridyls were also found in cigarette smoke (Schumacher et al., 1977; Sakuma et al., 1984; Heckman and Best, 1981).

Five methyl-2,3'-bipyridyls, including the 4- and 5-methyl-2,3'-bipyridyls, have been synthesized by the condensation of pyridine-3-diazonium chloride with either 4-methylpyridyl or 5-methylpyridyl (Frank and Crawford, 1959; Warfield et al., 1972), or by palladium catalyzed cross-coupling reactions (Ishikura et al., 1984; Bloom, 1990; Jacob et al., 1993). The 6-methyl-2,3'-bipyridyl has also been prepared by the latter methods. The 3-, 5- and 2'-methyl-2,3'-bipyridyls have been prepared by catalytic dehydrogenation in gas phase (Bowden, 1969). However, until the practice of the subject invention, the synthesis of 4'-, 5', and 6'-methyl-2,3'-bipyridyls had not been reported.

BRIEF SUMMARY

The subject invention provides materials and methods for reducing the fouling of surfaces exposed to aquatic environments. In a preferred embodiment, the practice of the subject invention reduces fouling by inhibiting the settlement of aquatic organisms. Advantageously, this can be achieved without the use of highly toxic compounds. Instead, compounds that deter attachment, but do not necessarily kill the organisms, are used.

In a preferred embodiment of the subject invention, pyridyl alkaloids are used to inhibit the settlement (attachment) of aquatic organisms to surfaces exposed to aquatic environments. The aquatic organisms whose settlement is inhibited according to the subject invention include, for example, barnacle larvae.

The compounds useful according to the subject invention include bipyridyls (2,3'-bipyridyls, 2,2'-bipyridyls, anabaseine and various anabaseine derivatives including, 3-benzylidene-anabaseine, and 3-cinnamylidene-anabaseine), tobacco alkaloids (including S- and R-nicotine, myosmine, S- and R-anabaseine and the tripyridyl nicotelline) and tetrapyridyls (nemertelline).

A further embodiment of the subject invention pertains to the development of economical syntheses of anabaseines and bipyridyls. Because of these unique synthesis procedures, the subject invention provides relatively inexpensive compounds. These compounds may be used, for example, as additives to marine paints. Advantageously, these compounds inhibit settlement without causing a generalized toxic effect on the aquatic environment.

In a specific embodiment of the subject invention, two bipyridyls-2,3'-BP and 2,2'-BP—have been found to be potent inhibitors of barnacle larval settlement.

Advantageously, the relatively low vertebrate toxicity of the bipyridyls and tetrapyridyl used according to the subject invention, make these pyridyl alkaloids and related analogs economical and effective antifouling additives for the protection of marine surfaces and other surfaces exposed to aquatic environments.

The pyridyl alkaloids of the subject invention have been found to potently inhibit the settlement of barnacle larvae. While some of these alkaloids are selectively toxic to crustaceans including barnacle larvae, others inhibit settlement in a manner that is not directly related to their crustacean toxicity.

Thus, in one embodiment, the subject invention provides additives for marine paints and other such coatings to be applied to surfaces exposed to aquatic environments. The subject invention further provides repellents and selective inhibitors for aquatic and/or terrestrial crustacean pests. In this embodiment, the compounds of the subject invention can be formulated in any appropriate manner for the control of the target pests.

DETAILED DISCLOSURE

Figure 1A:
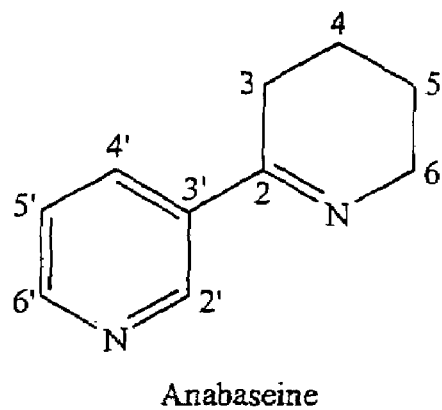
FIG. 1A shows the chemical structure of anabaseine.

The subject invention provides materials and methods for inhibiting the biofouling of surfaces exposed to aquatic environments. In one embodiment, the subject invention provides additives for marine paints and surface treatments. The subject invention further provides repellents and selective inhibitors for aquatic and/or terrestrial crustacean pests.

In a preferred embodiment, the practice of the subject invention prevents attachment of aquatic organisms, such as barnacle larvae, to surfaces exposed to aquatic environments. Advantageously, the inhibition of attachment can be achieved with compounds having decreased toxicity to aquatic environments as compared to current methods. Advantageously, the subject invention provides compounds that selectively inhibit settling of aquatic organisms.

In one embodiment the subject invention provides non-toxic additives for boat paints. Advantageously, the materials of the subject invention can be used to replace organotin additives that are toxic and whose application has been banned worldwide beginning in 2003. Furthermore, the materials of the subject invention are not expensive to make, are stable, are highly potent and selectively toxic to pests of commercial significance.

In a specific embodiment, the subject invention provides compositions for application to aquatic surfaces. Compounds of the subject can be formulated with surface treatments and applied directly to any surface exposed to an aquatic environment. Examples of surface treatments include, but are not limited to, paints, varnishes, stains, glosses, glazes, sealants, coatings, and coverings.

In a preferred embodiment of the subject invention, pyridyl alkaloids and related analogs are used as anti-settlement compounds to inhibit the attachment of aquatic organisms to aquatic surfaces. The compounds useful according to the subject invention include bipyridyls (2,3'bipyridyls, 2,2'bipyridyls, anabaseine and various anabaseine derivatives including 3-benzylidene-anabaseines and 3-cinnamylidene-anabaseine, tobacco alkaloids (including S- and R-nicotine, myosmine, S- and R-anabaseine and the tripyridyl nicotelline), tetrapyridyls (nemertelline), and related analogs and entantiomers. Analogs of 2,3'-BP include methyl substituted 2,3'-BP, for example, 4'-Me 2, 3'-BP, 5'-Me 2,3'-BP, 6'-Me 2,3'-BP, 3-Me 2,3'-BP, 4Me 2,3'-BP, 5-Me 2,3'-BP, and 6Me 2,3'-BP.

Other compounds useful according to the subject invention include those described in U.S. Pat. No. 5,977,144, which is incorporated herein in its entirety by reference. Advantageously, the relatively low vertebrate toxicity of the bipyridyls, tripyridyls, and tetrapyridyl used, according to the subject invention, make these pyridyl alkaloids and related analogs economical and effective antifouling additives for the protection of marine surfaces and other surfaces exposed to aquatic environments. Surfaces that can benefit from the invention include, but are not limited to, boats, piers, docks, buoys, locks, water intake pipes, drainage pipes, fish cages, and jettys.

The pyridyl alkaloids of the subject invention have been found to potently inhibit the settlement of barnacle larvae. While some of these alkaloids are selectively toxic to crustaceans including barnacle larvae, others inhibit settlement in a manner that is not directly related to their crustacean toxicity. Thus, these compounds are excellent antifouling agents that may be used as additives to ship paints and aquatic surface treatments, for example, varnishes, stains, glosses, glazes, sealants, coatings, and coverings.

In a specific embodiment of the subject invention, two bipyridyls-2,3'-BP and 2,2'-BP—have been found to be potent inhibitors of barnacle larval settlement. Since both are similarly lethal to nauplii after exposure for 24 hours, it is possible that they act upon a common receptor. However, these two compounds do not necessarily have the same mechanism of action. In this regard, it is noted that one is an effective metal chelator and the other is not. Specifically, for 2,3'-BP, there is a structure-activity relationship for inhibition that is not identical with that for acute crustacean toxicity or for interaction with vertebrate nicotinic receptors.

Anabaseine is a potent nicotinic agonist at most nicotinic receptors and it is able to produce a nicotine-like convulsive paralysis in insects and crustaceans. 2,3'-BP also can stimulate nicotinic receptors, but at relatively large concentrations. Because of the low basicity of 2,3'-BP (highest pKa is 4.4), only about one in one thousand molecules is ionized at pH 7.4, a common internal pH for vertebrate blood, and even fewer molecules are ionized at the pH of sea water, which is generally about 8.

At physiological pH, anabaseine exists in three different forms: a neutral cyclic imine form chemically similar to 2,3'-BP, a cyclic iminium protonated form, and an open-chain (amino-ketone) protonated form, in roughly equal concentrations (Zoltewicz, J., Bloom L., Kem, W. (1989) *J. Org. Chem.* 54:4462-4468; Zoltewicz, J., Bloom L., Kem, W. (1990) *J. Bioorg. Chem.* 18:395-412). On vertebrate nicotinic receptors, the cyclic iminium form was found to be the only one with significant activity (25; Kem, W. (2002), supra). In a preferred embodiment of the subject invention, it has been found that, for the nemertine alkaloids and their isomers, the un-ionized pyridyls are the most effective inhibitors of settlement. If the receptors are internal, then the postulated lack of ionization may enhance penetration to the internal receptor from the outside. If an inhibitor is to be of practical value as a paint additive, it would have to be able to enter the cyprid larvae from the outside environment.

The comparative potencies of various analogs summarized in Tables 1 and 2 suggest that there are several structural requirements for this activity. The presence of two heteroatoms in connecting rings is important for high potency, since phenylpyridine was essentially inactive. Clearly, a cisoid conformation is preferred, since 1,9-phenanthroline was as active as 2,3'-BP whereas the transoid 1,7-phenanthroline was not nearly as active.

TABLE 1

Larval settlement inhibition and lethal potencies of nemertine pyridyl alkaloids and related analogs

| Compound | Barnacle Larvae | | Crayfish Lethal Acute |
|---|---|---|---|
| | Settlement Inhibition $IC_{50}$ (µM) | Median Conc. $LC_{50}$ (µM) | Paralytic Dose $PD_{50}$ (µg) |
| Nemertine Alkaloids: | | | |
| 2,3'-BP | 4.1 (3.2-5.3) | 1.9 (1.0-4.3) | $0.88^1$ (0.71-1.1) |
| Anabaseine | 1.2 (0.91-1.7) | 2 | $3.6^1$ (3.1-4.1) |
| Nemertelline | 3.2 (1.8-6.0) | — | >120 |
| Anabasine | 3.0 (1.5-4.9) | — | 3.9 (3.4-4.5) |
| Bipyridyls: | | | |
| 2,3'-BP | 4.1 | 1.9 | $1.8^2$ (1.6-2.1) |
| 2,2'-BP | $7^3$ | 4.4 (2.9-6.2) | >100 |
| 2,4'-BP | >100 | >50 | >20 |
| 3,3'-BP | >100 | 10 | 17 (15-19) |
| 3,4'-BP | >100 | >20 | 61 (53-69) |
| 4,4'-BP | >100 | >50 | 11 (9.0-14) |
| Alkaloid Analogs: | | | |
| 1,9-phenanthroline | 2 | >50 | $3.0^2$ (2.2-4.1) |
| 1,7-phenanthroline | >50 | >50 | $>30^2$ |
| 2-(3-pyridyl)-pyrimidine | >50 | >50 | $2.6^2$ (2.1-3.2) |
| 3-Chloro-2,3'-BP | >100 | >50 | — |
| 2-(Thienyl)-pyridine | >100 | >100 | $650^2$ (540-770) |
| 2-(Phenyl)-pyridine | >100 | >100 | $520^2$ (400-690) |
| PTHP | >100 | >100 | $81^2$ (62-107) |
| 1-Methyl-2,3'BP | >100 | >100 | $>800^2$ |

[1]Data published previously using *P. clarkii* from California (Kem, W., Scott K., and Duncan J. (1976) Exper. 32: 684-686)
[2]Data published previously using *P. clarkii* from Louisiana (Kem, W., Soti, F. (2001) Hydrobiolog 456: 221-231)
[3]The inhibition of settlement data for this compound could not be fit by the probit method.

TABLE 2

Settlement inhibition and lethal potencies of the eight possible C-methyl 2,3'-bipyridyls.

| Compound | Barnacle Larvae Settlement | | Crayfish Paralysis | | Inhibition Pot/ Paralytic Pot |
|---|---|---|---|---|---|
| | % Inhib | Rel. Pot | $PD_{50}$ (µg) | Rel. Pot | |
| 2,3'-BP | 54 (11) | 100 | 1.8 (1.6-2.1) | 100 | 1.0 |
| 2'-Me2,3'-BP | 0 (33) | 0 | $210^1$ (160-260) | 1 | <0.05 |
| 4'-Me2,3'-BP | 90 (10) | 167 | $69^1$ (47-102) | 3 | 56 |
| 5'-Me2,3'-BP | 54 (28) | 100 | 3.3 (2.6-4.2) | 55 | 1.8 |
| 6'-Me2,3'-BP | 30 (16) | 56 | 12 (10-15) | 15 | 3.7 |
| 3-Me2,3'-BP | 34 (13) | 63 | $59^1$ (45-78) | 30 | 2.1 |
| 4-Me2,3'-BP | 83 (4) | 154 | 3.6 (2.9-4.4) | 50 | 3.1 |
| 5-Me2,3'-BP | 95 (5) | 176 | 0.98 (0.7-1.2) | 184 | 0.96 |
| 6-Me2,3'-BP | 16 (16) | 30 | 1.6 (1.2-2.2) | 112 | 0.27 |

[1]Data published previously (Kem, W., Soti, F. (2001) Hydrobiolog 456: 221-231)

Using methyl-substituted anabaseines, a structure-activity relationship has been delineated for several vertebrate nicotinic receptors consistent with the basic Beers-Reich model (Beers, W., Reich, E. (1970) *Nature* 228:917-922) for interaction with nicotinic cholinergic receptors. It has been found that a distance of approximately 5 Angstroms between an ionizable group and an H-bond electron donor is characteristic of nicotinic ligands displaying high affinity for the vertebrate muscle receptor.

2,3'-BP, like anabaseine, may stimulate nicotinic cholinergic receptors in the crustacean central nervous system. If this is so, then one would expect that methylation of 2,3'-BP would have an effect similar to that of methylation of anabaseine on vertebrate as well as crayfish receptors. While methylation can alter N atom basicity as well as introduce a bulky substituent, the steric hindrance and increased lipophilicity effects of methylation are expected to dominate. The C-methylations would not greatly affect the degree of ionization of 2,3'-BP at physiological pH.

Figure 1B:
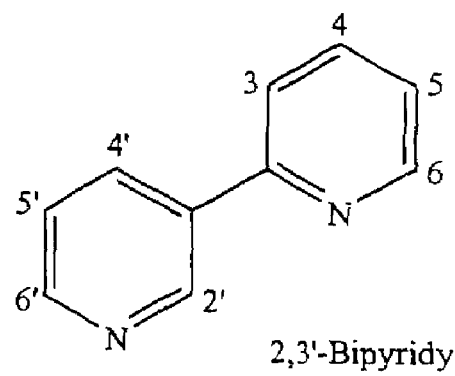
FIG. 1B shows the chemical structure of 2,3'-bipyridyl.
Figure 1C:
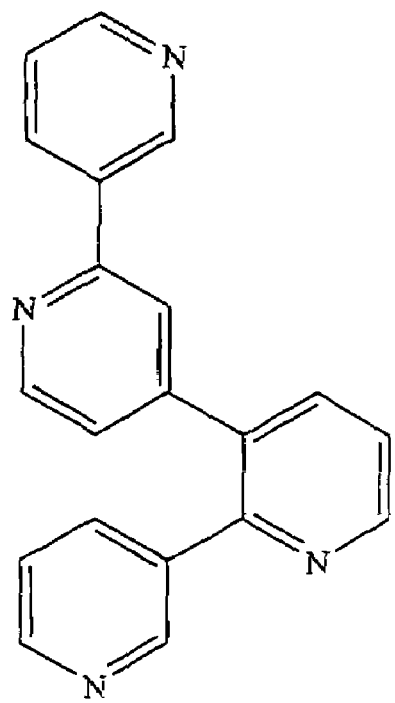
FIG. 1C shows the chemical structure of nemertelline.

In the methyl-anabaseine series, the site of methylation has been shown to greatly affect binding to vertebrate nicotinic receptors. Methyl substituents at the 2' and 4' positions of the 3-pyridyl ring greatly reduce nicotinic receptor activity, probably by preventing the optimal coplanar relationship of the two rings in anabaseine and 2,3'-bipyridyl. Positioning the methyl at the 3 position of the 2-pyridyl ring also reduces activity, but less than the previously mentioned substitutions. While the methyl substitution dependence of crayfish paralytic activity (Table 2) was very similar to that for vertebrate nicotinic receptors, the enhancing effect of methylation at the 4' position upon barnacle larval settlement was unique. The high anti-settlement activity of this compound, and also of 1,9-phenanthroline and nemertelline (FIG. 1C), suggests that there is some action of the 2,3-BPs that is unrelated to an effect upon nicotinic receptors. One possible non-cholinergic site would be the pyridyl chemoreceptors documented to occur in some other crustaceans.

A variety of nemertine pyridyl alkaloids were tested for inhibition of barnacle (*Balanus amphitrite*) larval settlement and for crustaceans. Eight C-methylated 2,3'-BP isomers were prepared to determine where substitution is permitted without loss of activity. It was determined that anti-settlement and toxicity activities were not always related. For instance, 4'-methyl-2,3'-BP displayed only 3% of the crayfish paralytic activity of 2,3'-BP but inhibited settlement almost 2-fold more effectively. Two other isomers displaying exceptional anti-settlement activity were the 4- and 5-methyl-2,3'-BPs; these also displayed high crustacean toxicity. Nemertelline inhibited barnacle settlement at concentrations similar to 2,3'-BP but was 136-fold less toxic when injected into crayfish. Nicotelline, a tripyridyl, displayed an activity similar to nemertelline. Thus, certain bipyridyls and tetrapyridyis can be used according to the subject invention as anti-fouling additives.

A further embodiment of the subject invention pertains to the development of economical syntheses of anabaseines and bipyridyls. One of the most attractive aspects of these compounds as anti-settlement additives is their structural simplicity and ease of chemical synthesis. Many substituted bipyridyls have already been synthesized and investigated. However, syntheses of all eight possible C-methyl isomers of 2,3'-bipyridyl have not been known until the subject invention. In a specific embodiment of the current invention, a method to synthesize the 4'-, 5'- and 6'-methyl-2,3'-bipyridyls is disclosed. Advantageously, the precursor materials, methyl-anabaseines, for the formation of the 4',5'- and 6'-methyl-2,3'-bipyridyls are commercially available. Because of these unique synthesis procedures, the subject invention provides relatively inexpensive compounds, which can be utilized as additives to aquatic surface treatments and paints.

Although other natural products that are potent inhibitors of settlement are known, they are not as attractive as commercial products. They are less attractive because they have more complicated structures; this makes them much more expensive to produce. Also, their environmental fates and effects are more difficult to determine.

A further embodiment of the subject invention is directed to methods of initiating paralysis in humans and animals. This specific embodiment is beneficial in clinical settings where a patient is required to be still while undergoing medical treatments. One method of initiating paralysis comprises injecting a patient with a sufficient amount of a composition of a pharmaceutically acceptable carrier and a pyridyl alkaloid, a pharmaceutically acceptable salt or analog thereof. A pyridyl alkaloid is selected from the group consisting of 2,3'-bipyridyl, 2,2'-bipyridyl, anabaseine, 3-benzylidene-anabaseine, 3-cinnamylidene-anabaseine, S-nicotine, R-nicotine, myosmine, S-anabasine, R-anabasine, nicotelline, nemertelline, 1-9-phenanthroline, 4'-Me2,3'-bipyridyl, 5'-Me2,3'-bipyridyl, 6'-Me2,3'bipyridyl, 3-Me2,3'-bipyridyl, 4-Me2,3'-bipyridyl, 5-Me2,3'-bipyridyl, 6-Me2,3'-bipyridyl, 2,4'-bipyridyl, 3,3'-bipyridyl, 3,4'-bipyidyl, 4,4'-bipyridyl, 2-(3-pyridyl)-pyrimidine, 2'-Me2,3'-bipyridyl, and salts, analogs, enantiomers and mixtures thereof.

MATERIALS AND METHODS

Compounds 2,3'-Bipyridyl (2,3'-BP), 2-(thienyl)-pyridine and 2-(phenyl)-pyridine were purchased from Aldrich Chemical Company. The C-methyl-2,3'-bipyridyls were prepared from the corresponding methylanabaseines by dehydrogenation. Description of the synthesis of 1-methyl-2,3'-BP has been reported (Zoltewicz, J., Bloom L., Kem, W. (1992) *J. Org. Chem.* 57:2392-2395). Compounds were purified by silica gel chromatography as their free bases, and were homogeneous as evaluated by silica gel TLC, reversed phase HPLC and NMR analysis methods.

Biological Assays

Adult freshwater crayfish *Procambarus clarkii* obtained from Louisiana were used as previously described (Kem W., Abbott, B., Coates, R. (1971), supra; Kem, W. (1971), supra; Kem, W., Scott K., and Duncan J. (1976), supra). Each alkaloid, dissolved in 0.9% sodium chloride containing 10 mM Tris buffer (pH 7.4), was injected into the haemocoele which surrounds the heart. Dose per unit weight was kept constant by injecting a variable volume, 0.10 ml per 10 g fresh weight. Paralysis was measured 15 minutes after injection by measuring the animal's ability, after being placed on its back, to right itself within a 2-minute period. Although the convulsive paralytic effect of the bipyridyls reached a peak about 2-minutes after injection, paralysis could be more conveniently measured 15 minutes after injection. Generally, the same number (10-20) of crayfish were injected at each dose, and the dose interval was kept constant. Before the assay, crayfish were tested to ascertain that they could right themselves within a one minute period. The median paralytic dose ($PD_{50}$) was calculated using the Spearman-Karber statistical method (Kem W., Abbott, B., Coates, R. (1971), supra).

The barnacle larval 24 hour settlement and toxicity assays were carried out using previously described protocols (Rittschof, D., Clare, A., Gerhart, D., Mary S., Bonaventura, J. (1992) *Biofoul* 6:115-122; Sasikumar, N., Clare, A., Gerhart, D., Stover, D., Rittschof, D. (1995) *Bull. Environ. Contam. Toxicol.* 54:289-296). While the cypris larval stage was used in settlement tests, the second naupliar larval stage was used in toxicity tests. Great care was taken to ensure that the free bases completely dissolved in aged sea water solutions previously filtered to remove particles >than 100 kDa. This was accomplished by diluting (by immediate and thorough vortexing) a $3\times10^{-2}$ Molar solution of the free base in methanol at least 1,000-fold into the filtered sea water. Diluted aqueous solutions of the compounds were not refrigerated and were used within an hour of preparation.

All patents, patent applications, provisional applications, and publications referred to or cited herein are incorporated by reference in their entirety, including all figures, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Inhibition of Barnacle Cyprid Settlement

Figure 2:
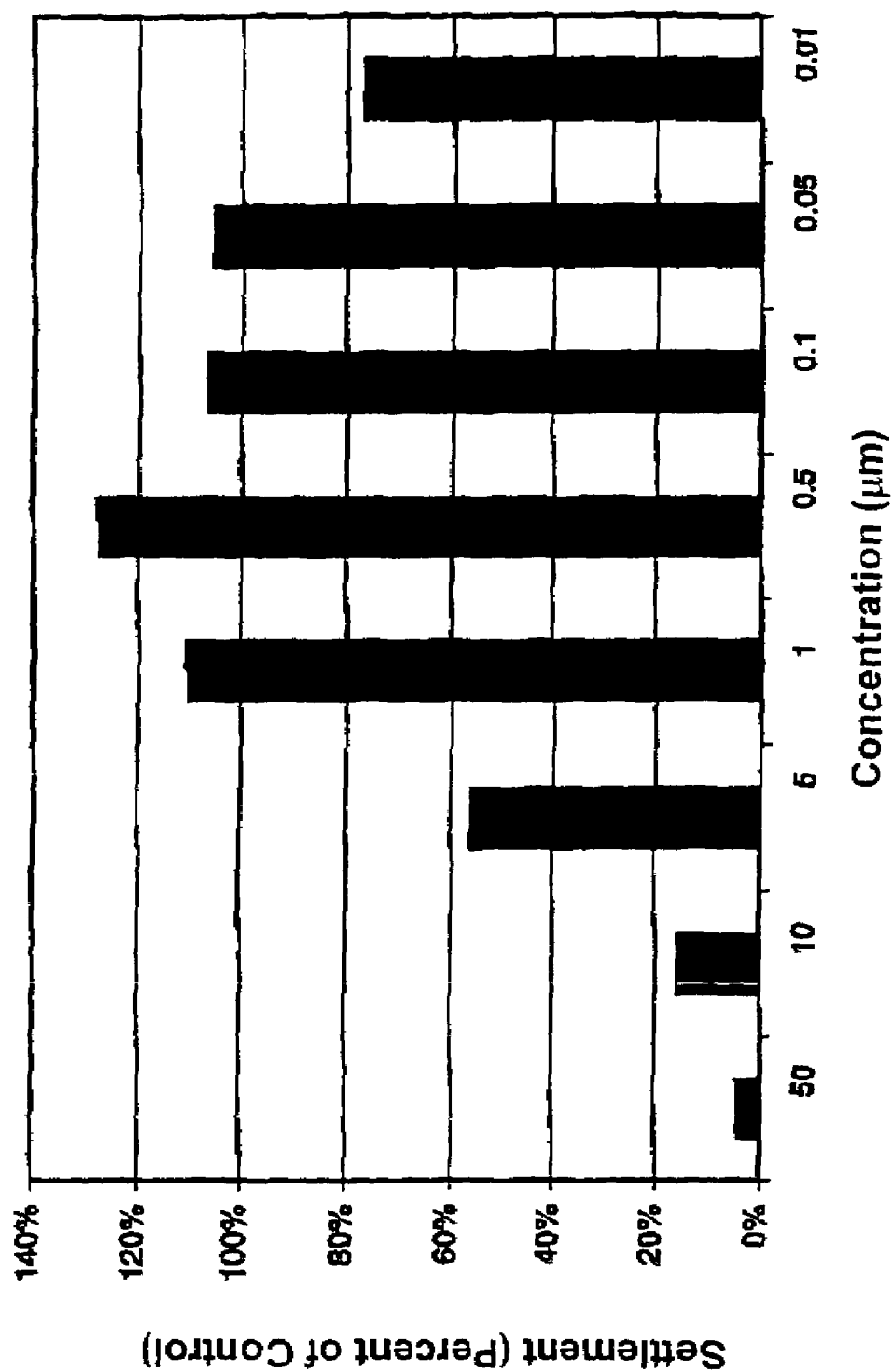
FIG. 2 shows histogram of barnacle (*B. amphitrite*) cyprid settlement inhibition by anabaseine, a minor alkaloid of *A. angulatus* and the major alkaloid of the tobacco plant *Nicotiana glauca* (the source of the (S)-anabaseine used in Example 1). Settlement was measured after 24 hr exposure to anabaseine. The $IC_{50}$ for anabaseine inhibition of settlement in Table 1 was calculated from a probit analysis of this data.

The initial assays with the nemertine alkaloids showed that these 3-substituted pyridly alkaloids were able to inhibit settling at micromolar concentrations (Table 1). These included anabaseine and 2,3'-BP. Nemertelline also inhibited larval settlement. This tetrapyridyl is essentially composed of two 2,3'-BP moieties. (S)-anabaseine (FIGS. 1, 2) also inhibited settlement.

All six possible unsubstituted bipyridyls were also tested. The assays (Table 1) showed that 2,3'-BP potently inhibited barnacle settlement and was also the most toxic as evaluated by barnacle naupliar 24 hr mortality and 15 minute crayfish paralysis. 2,2'-BP inhibited settlement at only slightly higher concentrations, and its 24 hour naupliar toxicity was also slightly less, but it displayed a remarkably low toxicity on crayfish as measured by the paralysis assays. The other four BPs displayed very weak ability to inhibit larval settlement, relative to these two isomers.

Various analogs of 2,3'-BP were then tested to determine what molecular features are important for anti-settlement activity. Amongst these compounds 1,9-phenanthroline, a rigid analog containing the "cisoid" conformation of 2,3'-BP, was almost as active as 2,3'-BP. In contrast, 1,7-phenanthroline, a rigid analog containing the "transoid" conformation of 2,3'-BP, was inactive at a 10-fold higher concentration. These differences indicate that the most biologically effective conformation of 2,3-BP is cisoid, where the two nitrogen atoms are oriented on the same side of the planar molecule.

The inactivity of 2-(phenyl)-pyridine indicates that both nitrogen atoms of 2,3'-BP are important for this activity. The inactivity of the 2-(thienyl)-pyridine indicates that a sulphur heteroatom will not effectively replace the one nitrogen in 2,3'-BP. The inability of the 3-chloro-2,3'-BP to inhibit settlement at 100 µM contrasts with the relatively small loss of activity when a methyl group is attached at this position (Table 2). Since the chlorine atom is not too different in size from the methyl group, it seems that the electron-withdrawing property of the chlorine is detrimental to activity; the methyl group in contrast would be electron-donating and would increase the basicity of the nitrogen on the 2-pyridyl ring of 2,3'BP.

PTHP (full name: 2-(3-pyridyl)-3,4,5,6-tetrahydropyrimidine) is a permanently charged analog of anabaseine and 2,3'-BP; its relative inactivity indicates that protonation of the 2-pyridyl ring nitrogen inhibits activity. The low anti-settlement activity of another permanently ionized analog, 1-methyl-2,3'-BP, is also consistent with this interpretation.

The relative abilities of the eight possible C-methylated 2,3'-BPs to inhibit settlement were determined at a single concentration in three separate experiments, as shown in Table 2. What was most remarkable was the enhanced anti-settlement potency of the 4'-Me-BP and, as a result of the same substitution, a greatly reduced (33-fold) acute crayfish toxicity. Placement of a methyl at either the 4 or 5-positions of the 2-pyridyl ring also elevated anti-settlement activity. Additionally, one observes that placement of a methyl group at either of the ortho-(2' or 6') positions of the 3-pyridyl ring reduced anti-settlement activity, particularly when a methyl substituent was added at the 2'-position.

EXAMPLE 2

Crayfish Paralytic Activities

Crayfish paralysis is a simple bioassay which allows quantitative comparison of the acute neurotoxicity of a variety of toxins (Kem W., Abbott, B., Coates, R. (1971), supra). It has been particularly useful for examining nicotinic compounds, since these receptors are mostly located within the central nervous system; where electrophysiological recordings of synaptic responses generated by nicotinic receptors are more difficult (Wiersma, C., Schallek, W. (1946) *J. Neurophysiol* 10:23-38; Prosser, C. (1940) *J. Cell Comp. Physiol.* 16:25-38). Since the crustacean nervous system does not seem to possess an equivalent of the vertebrate blood: brain barrier, chemicals injected into the systemic circulation should readily reach the central nervous system (Abbott, N. (1970) *Nature* 225:291-293).

Injected anabaseine and 2,3'-BP both caused a remarkably rapid convulsive paralysis of crayfish and other crustaceans. Animals initially develop tremors, then flex their legs, repeatedly flip their tails, then fall on their side in a tonic convulsion within 2-5 minutes after injection. Recovery is appreciable within 15 minutes, the time selected as most convenient for evaluating groups of 5 animals rapidly injected one after another. Thus the median paralytic doses reported in the two tables are actually more than twice the $PD_{50}$ values which would be obtained at minute post-injection, with the exception of nemertelline. 2,2'-BP was at least 50-fold less toxic than 2,3'-BP when measured by this bioassay. Nemertelline was about 140-fold less paralytic than 2,3'-BP. Anabaseine was approximately 4-fold less paralytic than 2,3'-BP or anabaseine.

The most paralytic alkaloid analogs were 1,9-phenanthroline and 2-(3-pyrimidinyl)-pyridine, whose structures are very similar to that of 2,3'-BP. These compounds also are un-ionized at physiological pH. The low activity of the transoid isomer 1,7-phenanthroline indicates that paralysis, like settlement inhibition, is affected by the cisoid conformation of 2,3'-BP. Anabaseine was slightly less paralytic than 2,3'-BP; this may be due to its occurrence in several forms at physiological conditions. The permanently ionized analogs of 2,3'-BP (PTHP and 1-methyl-2,3'-BP) displayed very low paralytic activity as well as anti-settlement activity.

The effects of individually replacing each hydrogen atom in 2,3'-bipyridyl with the more bulky methyl substituent was also investigated. In Table 2 one observes the methylation of carbons adjacent to the ring-joining carbons (2',4' and 3) greatly reduced paralytic activity, as has also been observed for methyl-anabaseine stimulation of nicotinic receptors in vertebrates. On the other hand, methyl substitution at the 4,5 and 6 positions of the 2-pyridyl ring and the 5' and 6' positions of the 3-pyridyl ring did not greatly affect paralytic potency. In one instance (5 position), methylation even increased paralytic potency almost 2-fold. Thus, the effects of methylating 2,3'-BP on crayfish paralytic activity were in some instances quite different from what was observed for inhibition of barnacle larval settlement.

EXAMPLE 3

General Synthesis of Methyl-2,3'-bipyridyls

A mixture of methyl-anabaseine free base (35 mg, 0.2 mmole) and N-chlorosuccinimide (67 mg, 5 mmole) in carbon tetrachloride (5 ml) was stirred overnight at room temperature. Water (3 ml) and sodium hydrogen carbonate (0.3 g) were added, separated and the aqueous phase was extracted with carbon tetrachloride (2×1 ml). The combined organic phases were dried (magnesium sulfate) and evaporated under vacuum giving the methyl-3,3-dichloro-anabaseines in 68-98% yield. These intermediates were pure enough by TLC and $^1$H-NMR for the next step. The above methyl-3,3-dichloro-anabaseines were dissolved in a solution of sodium methoxide in dry methanol (0.5 ml of a 2M solution, 1.0 mmole) and stirred at room temperature overnight. After evaporation in vacuum to the residue water (2 ml) was added and extracted with dichloromethane (5×1 ml). The combined organic solutions were dried (magnesium sulfate), decolorized (activated carbon), and evaporated in a vacuum (2 mm Hg, 45° C.) giving the pure methyl-2,3'-bipyridyls as light brown oils in 64-84% yield.

Specifically, the yields for 4'-Methyl-2,3'-bipyridyl, 5'-Methyl-2,3'-bipyridyl, and 6'-Methyl-2,3'-bipyridyl are 72%, 64%, and 84% respectively in applying the process of the subject invention.

In addition, the NMR data of the dichloro intermediates and the methyl-bipyridyls are presented in Tables 3 and 4, respectively, while the GC and MS data of methyl-bipyridyls are presented in Table 5.

TABLE 3

NMR data of 3,3-dichloro-2,3'-bipyridyl and its methyl derivatives

| Compound | 2' | 4' | 5' | 6' | 4 | 5 | 6 | CH₃ |
|---|---|---|---|---|---|---|---|---|
| 3,3-Dichloro-2,3'-BP | 9.17, d* 1.8 | 8.37, ddd 8.1, 1.8, 1.5 | 7.39, ddd 8.1, 5.1, 0.6 | 8.65, dd 5.1, 1.5 | 2.75-2.81, m | 2.00-2.10, m | 3.98, dd 6.0, 6.0 | — |
| 3,3-Dichloro-2'-Me-BP | — | 7.96, dd 7.8, 1.8 | 7.18, dd* 7.8, 5.1 | 8.53, dd 5.1, 1.8 | 2.76-2.82, m | 2.03-2.12, m | 3.94, dd 6.0, 6.0 | 2.56, s |
| 3,3-Dichloro-4'-Me-BP | 8.88, s | — | 7.46, d 5.4 | 8.57, d 5.4 | 2.78-2.84, m | 2.05-2.14, m | 3.97, dd 6.0, 5.7 | 2.46, s |
| 3,3-Dichloro-5'-Me-BP | 9.00, d* 1.5 | 8.13, s* | — | 8.48, d* 1.5 | 2.74-2.80, m | 2.00-2.10, m | 3.97, dd 6.0, 5.7 | 2.41, s* |
| 3,3-Dichloro-6'-Me-BP | 9.04, d 2.1 | 8.19, dd 8.1, 2.1 | 7.18, d 8.1 | — | 2.74-2.80, m | 1.99-2.08, m | 3.95, dd 6.0, 5.7 | 2.61, s |
| 3,3-Dichloro-4-Me-BP | 9.12, d* 1.8 | 8.30, ddd 8.1, 1.8, 1.8 | 7.34, ddd 8.1, 4.8, 0.9 | 8.62, dd 4.8, 1.8 | 2.43-2.56, m (1H) | 1.74-1.98, m (2H) | 4.17, ddd, (1H) 19.5, 5.4, 1.8 3.79, ddd, (1H) 19.5, 10.8, 6.0 | 1.39, d 6.6 |
| 3,3-Dichloro-5-Me-BP | 9.15, d* 2.1 | 8.29, ddd 8.1, 2.1, 1.5 | 7.32, ddd 8.1, 4.8, 0.6 | 8.64, dd 4.8, 1.5 | 2.85-2.91, m (1H) 2.28-2.37, m (1H) | 2.28-2.37, m (1H) | 4.16-4.26, m (1H) 3.24-3.36, m (1H) | 1.07, d 5.7 |

First row: chemical shift in ppm and its splitting,
*line broadening or further unresolved small long range coupling(s);
second row: coupling constant(s) in Hz.
In parentheses: the number of hydrogen(s), if it is necessary.

TABLE 4

NMR data of 2,3-bipyridyl and its methyl derivatives

| Compound | 2' | 4' | 5' | 6' | 3 | 4 | 5 | 6 | CH₃ |
|---|---|---|---|---|---|---|---|---|---|
| 2,3'-BP | 9.20, dd 2.4, 0.9 | 8.33, ddd 7.8, 2.4, 1.8 | 7.41, ddd 7.8, 4.8, 0.9 | 8.66, dd 4.8, 1.8 | 7.74-7.84, m | 7.74-7.84, m | 7.30, ddd 6.9, 4.8, 1.8 | 8.73, ddd 4.8, 1.8, 1.2 | — |
| 2'-Me-BP | — | 7.73, dd 7.8, 1.8 | 7.23, dd* 7.8, 4.8 | 8.55, dd 4.8, 1.8 | 7.43, ddd 7.8, 1.2, 0.9 | 7.78 7.8, 7.8, 1.8 | 7.30, ddd 7.8, 4.8, 1.2 | 8.73, ddd 4.8, 1.8, 0.9 | 2.61, s |
| 4'-Me-BP | 8.59, s* | — | 7.21, d* 4.8 | 8.49, d 5.1 | 7.43, ddd 7.8, 1.2, 0.9 | 7.80 7.8, 7.5, 1.8 | 7.31, ddd 7.5, 4.8, 1.2 | 8.73, ddd 4.8, 1.8, 0.9 | 2.41, s |
| 5'-Me-BP | 8.98, d 2.1 | 8.15, s* | — | 8.48, d* 1.8 | 7.71-7.81, m | 7.71-7.81, m | 7.27, ddd 6.6, 4.8, 1.8 | 8.71, ddd 4.8, 1.5, 1.2 | 2.41, s |
| 6'-Me-BP | 9.07, d 2.1 | 8.22, dd 8.1, 2.4 | 7.23-7.29, m | — | 7.69-7.80, m | 7.69-7.80, m | 7.23-7.29, m | 8.70, ddd 4.8, 1.8, 1.2 | 2.62, s |
| 3-Me-BP | 8.80, dd 2.4, 0.6 | 7.89, ddd 7.8, 2.4, 1.8 | 7.40, ddd 7.8, 4.8, 0.6 | 8.64, dd 4.8, 1.8 | — | 7.62, dd* 7.8, 0.9 | 7.24, dd 7.8, 4.8 | 8.56, dd* 4.8, 0.9 | 2.39, s |
| 4-Me-BP | 9.17, dd 2.4, 0.9 | 8.31, ddd 7.8, 2.4, 1.5 | 7.39, ddd 7.8, 4.8, 0.9 | 8.64, dd 4.8, 1.5 | 7.56, s* | — | 7.12, d* 5.1 | 8.57, dd 5.1, 0.6 | 2.44, s |
| 5-Me-BP | 9.17, dd 2.4, 0.9 | 8.28, ddd 8.1, 2.4, 1.8 | 7.37, ddd 8.1, 4.8, 0.9 | 8.61, dd 4.8, 1.8 | 7.55-7.66, m | 7.55-7.66, m | — | 8.53-8.55, m | 2.37, s* |
| 6-Me-BP | 9.18, dd 2.4, 0.9 | 8.30, ddd 8.1, 2.4, 1.8 | 7.37, ddd 8.1, 4.8, 0.9 | 8.62, dd 4.8, 1.8 | 7.52, d* 7.8 | 7.65, dd 7.8, 7.5 | 7.13, d* 7.5 | — | 2.62, s |

First row: chemical shift in ppm and its splitting;
*Line broadening or further unresolved small long range coupling(s);
second row coupling constant(s) in Hz.

TABLE 5

GC retention time and MS data of 2,3-bipyridyl and its methyl derivatives

| | 2,3'-BP | 2' | 4' | 5' | 6' | 3 | 4 | 5 | 6 |
|---|---|---|---|---|---|---|---|---|---|
| CH₃ Position (m:s) | | | | | | | | | |
| m/z | 12:16 | 12:17 | 12:43 | 13:19 | 12:52 | 12:43 | 13:15 | 13:21 | 12:46 |
| 51 | 5.3 | | 6.5 | 7.8 | 7.7 | | 6.6 | | |
| 63 | | 5.4 | 5.3 | 5.3 | | | 6.5 | 5.1 | |
| 65 | | | | | 7.1 | 7.0 | 8.0 | | |
| 75 | | | | | | | | | 5.1 |
| 78 | | | 8.2 | 8.1 | | | | | |
| 79 | | | | | 6.4 | | | | |

TABLE 5-continued

GC retention time and MS data of 2,3-bipyridyl and its methyl derivatives

| | | | | CH$_3$ Position | | | | | |
|---|---|---|---|---|---|---|---|---|---|
| | 2,3'-BP | 2' | 4' | 5' | 6' (m:s) | 3 | 4 | 5 | 6 |
| m/z | 12:16 | 12:17 | 12:43 | 13:19 | 12:52 | 12:43 | 13:15 | 13:21 | 12:46 |
| 89 | | | 5.4 | | | | | 5.8 | |
| 92 | | | | | | | 7.4 | 5.5 | 6.6 |
| 104 | | | 5.2 | | | | | | |
| 115 | 9.5 | 15.6 | 9.7 | 8.0 | 11.1 | | 11.4 | 13.7 | 11.2 |
| 117 | | | 7.0 | 7.9 | 5.8 | | | | |
| 118 | | | | | | | | 5.3 | |
| 128 | | | 7.7 | 8.3 | | | | | |
| 130 | | | | | | | | 19.0 | |
| 141 | 5.1 | 6.5 | 10.1 | 6.5 | 5.4 | | | | 5.6 |
| 142 | 12.1 | 12.3 | 19.6 | 15.8 | 21.3 | | 12.0 | 13.3 | 12.9 |
| 143 | | | 12.7 | 8.4 | | 5.2 | 6.9 | 9.4 | |
| 144 | | | 10.1 | 7.3 | | 32.1 | 36.9 | 23.1 | |
| 155 | | | 34.6 | 40.8 | | 9.2 | | | |
| 156 | | | | 5.3 | | | | | |
| 168 | 15.8 | 14.3 | 6.8 | 5.6 | 11.5 | | 9.1 | 6.7 | 5.5 |
| 169 | 100.0 | 100.0 | 65.4 | 61.7 | 100.0 | | 72.5 | 77.6 | 68.8 |
| 170 | 19.6 | 19.6 | 100.0 | 100.0 | 15.0 | | 100.0 | 100.0 | 100.0 |
| 171 | | | 16.6 | 16.2 | | | 15.3 | 15.5 | 12.7 |

EXAMPLE 4

Synthesis of 3-Hydroxymethyl-2,3'-bipyridyl

To a continually stirred, ice-cold solution of 2,3'-bipyridine-3-carboxylic acid (0.28 g, 1.40 mmole) in dry tetrahydrofuran (10 ml) and triethylamine (0.20 ml, 1.43 mmole) ethyl chloroformate (0.14 ml, 1.46 mmole) was added drop-by-drop over a 30 minute period. The precipitated product was then filtered and washed several times with tetrahyrofuran (3×2 ml). The THF phases were combined, cooled to +10° C., and while stirring under an argon atmosphere, sodium borohydride (0.185 g, 4.9 mmole) was added and then methanol (0.90 ml, 22.2 mmole) was added drop-by-drop over a 1 hour period during which time the temperature increased to 20° C. (Soai et al., 1987). The material was stirred for an additional 1 hour at room temperature. Then, 1N hydrochloric acid was carefully added, the solvent was evaporated under vacuum to 5 ml and washed with dichloromethane (3×5 ml). Sodium carbonate (0.85 g) was added to the aqueous phase, which was then extracted with dichloromethane. The combined fractions were dried with magnesium sulfate and evaporated under vacuum (2 Hg mm, 45° C.) giving a pure product (0.22 g, 84%). $^1$H-NMR, δ, ppm, 8.71 (1H, dd, J=2.1, 0.6 Hz, C2'-H), 8.55 (1H, dd, J=4.8, 1.5 Hz, C6-H), 8.52 (1H, dd, J=4.8, 1.8 Hz, C6'-H), 7.95 (1H, dd, J=7.8, 1.5 Hz, C4-H), 7.91 (1H, ddd, J=7.8, 2.1, 1.8 Hz, C4'-H), 7.35 (1H, ddd, J=7.8, 4.8, 0.6 Hz, C5'-H), 7.31 (1H, dd, J=7.8, 4.8 Hz, C5-H), 4.58 (2H, s, CH$_2$-O).

EXAMPLE 5

Synthesis of 3-Methyl-2,3'-bipyridyl

A 3-hydroxymethyl-2,3'-bipyridyl (42.3 mg, 0.227 mmole) solution containing methanol (5 ml) and 4N solution of hydrogen chloride in dry 1,4-dioxane (0.57 ml, 2.3 mmole) was hydrogenated in the presence of palladium on activated carbon catalyst (10%, 40 mg) at room temperature and ambient pressure for 3 hours. The catalyst was filtered off, washed with methanol (3×1 ml), and the combined methanolic solutions were evaporated under vacuum. The residue was dissolved in water (2 ml), sodium carbonate was added (0.1 g) and the solution was extracted with dichloromethane (3×2 ml). The combined dichloromethane solutions were dried (magnesium sulfate) and rotary evaporated at 2 mm Hg-45° C., giving the pure product (29.4 mg, 76%) as a colorless oil.

It should be understood that the examples and embodiments described herein are for illustrative purposes only and that various modifications or changes in light thereof will be suggested to persons skilled in the art and are to be included within the spirit and purview of this application.

We claim:

1. A compound which is 4'-Me2,3'-bipyridyl.

\* \* \* \* \*